(12) United States Patent
Chang et al.

(10) Patent No.: US 8,946,503 B2
(45) Date of Patent: Feb. 3, 2015

(54) HNRNP A1 KNOCKOUT ANIMAL MODEL AND USE THEREOF

(71) Applicant: Kaohsiung Medical University, Kaohsiung (TW)

(72) Inventors: Yung-Fu Chang, Kaohsiung (TW); Ting-Yuan Liu, Kaohsiung (TW); Yuh-Jyh Jong, Kaohsiung (TW); Jan-Gowth Chang, Kaohsiung (TW)

(73) Assignee: Kaohsiung Medical University, Kaohsiung (TW)

( * ) Notice: Subject to any disclaimer, the term of this patent is extended or adjusted under 35 U.S.C. 154(b) by 0 days.

(21) Appl. No.: 14/092,678

(22) Filed: Nov. 27, 2013

(65) Prior Publication Data

US 2014/0123329 A1    May 1, 2014

Related U.S. Application Data

(63) Continuation of application No. 13/600,635, filed on Aug. 31, 2012, now abandoned.

(60) Provisional application No. 61/534,396, filed on Sep. 14, 2011.

(51) Int. Cl.
*A01K 67/027* (2006.01)
*G01N 33/50* (2006.01)
*C12N 15/85* (2006.01)

(52) U.S. Cl.
CPC ........ *A61K 67/0276* (2013.01); *G01N 33/5011* (2013.01); *G01N 33/5088* (2013.01); *G01N 22/6896* (2013.01); *C12N 15/85* (2013.01); *G01N 2800/28* (2013.01); *G01N 2800/7042* (2013.01)
USPC ............................................................ 800/9

(58) Field of Classification Search
None
See application file for complete search history.

*Primary Examiner* — Robert M Kelly
(74) *Attorney, Agent, or Firm* — Hannah M. Tien

(57) ABSTRACT

A nucleic acid construct comprising a genetic engineered heterogeneous nuclear ribonucleoprotein (hnRNP) A1 gene is provided. A transgenic mouse in which the expression of hnRNP A1 gene has been disrupted is also provided. The mouse is useful for studying the role of hnRNP A1 gene in normal and disease states of a developmental disorder and muscular diseases. Therefore, a method of screening a compound for potential use in prevention and/or treatment of developmental disorder and muscular diseases is further provided.

1 Claim, 6 Drawing Sheets

```
                             SEQUENCE LISTING

<160> NUMBER OF SEQ ID NOS: 7

<210> SEQ ID NO 1
<211> LENGTH: 34
<212> TYPE: DNA
<213> ORGANISM: Bacteriophage P1
<220> FEATURE:
<221> NAME/KEY: protein_bind
<222> LOCATION: (1)..(34)

<400> SEQUENCE: 1
ataacttcgt ataatgtatg ctatacgaag ttat                              34

<210> SEQ ID NO 2
<211> LENGTH: 20155
<212> TYPE: DNA
<213> ORGANISM: Mus musculus
<220> FEATURE:
<221> NAME/KEY: gene
<222> LOCATION: (1)..(20155)

<400> SEQUENCE: 2
gctgtataga cacttaagat tattatgtcc tcttgatgaa ttgattcttt aattaactag    60
cctgctgtta tttgcccaac atatctcata ggtctgttat ggaaaaagaa ttaagagagc   120
actttggaaa cagaggcaaa agtttaacaa taaggaagt taaaaaataa ctttaatgaa    180
ttttctgaac tatctgtaat tttatctctg ctgtctccaa ctactcaaat aaacgaggtt   240
tactatgttt tatcagatct ttagacataa tttactattg aaagatactg agcaaattac   300
cggtatatca ccctccacag ctctgtacaa ctgaatctta atgatttagg gatgagaaca   360
aggcacactg agttcaagga tttgcttcag aaaccagagt taagatttcc cagcttgtta   420
gctgacctct ttagtacagg gcattttatt ccaacataat tatacctgtt ggctcagatg   480
caaatttgct gtattcagag gaatgtagat tacaatcagg gagtacttga gttcaacgtg   540
cttgcttggc tccgtggaga agatgggagt actatttgtt atgactgacc ttgaagaaat   600
cttttcaagt acatcttgtc aatctcatgt gtgtataagc tatgaagcat aatacaacac   660
acactcagaa aatctgtaaa ttaaaactgc acatgaagat ctttattcca tctatgacct   720
attttaaggt agaaaaaatg tgccagtgct taattctgat gaagtactta ttactggaaa   780
ggaaagttca gaaaatatgg ctcccaaatt cactaggaag ggagaaaatg gtctggccaa   840
ctcactacac tttttaaaaa gagtttatgc atatatttaa gtacaggttt gtctgtctgt   900
attaatagtc caaggagctg aaaaatcaac cagcaatcaa gtatttgcct ctcaagttct   960
aggcaaaaat gacaggacta taatggtcaa atgttagaat aaattttta ttattgttgt   1020 tgttgctatt attattatta ttattattat tattgagaaa gggtcttact aacataactt   1080
tagttgggct gaagctgggt atatagacta ggctaagaaa tcccactgtc cctgcttccc   1140
aactgtagga attaaaaggc atgcaggacc aggctctgct tgatttgtag ttttaattat   1200
tgtcgttaaa aaaaaaaaaa gaagagttca agggccagcc tggtctacga aaaagatca   1260 aggatagcca ggattaacag agaaagtgtc ttgaataata aataaataaa taaataaata   1320
aataagcaag caagcatgct ttgagaatga gttcaaggtc tgcctttcta cttagtgact   1380
gactagtttc aaaattaaat tcaagccggg cgtggtggcg cattccttta atcccagcac   1440
```

```
ttgggaggca gaggcaggcg gttttctgag ttcgaggcca gcctggtcta caaagtgagt    1500
tccaggacag ccaggcctac acagagaaac tctgtctcga aaaccaaaa aaaaaaaaaa    1560 cagccaagta tggtgacatg aacctttaa tttcagcact tatggatttc tgggagttgg    1620
atggaggcca gcttcattta tatgcaaat tctagaatgt ccagagctac ataacagagt    1680
tcctgcctca aaataaata aaacaggct ggtgagacgg ctcagtgggt aagagcaccc    1740
gactgctctt ccgaaggtcc ggagttcaaa tcccagcaac cacatggtgg ctcacaacca    1800
tccataacga gatctgactc cctcttctgg agtgtctgaa gacagctaca atgtacttac    1860
atataataaa taaataaata aataaataaa taaataaaac cacgtttgtg gcctggacag    1920
atagcttagt gacttcttag agtggtagct gcaatctagg cagtggtggt ccatgccttt    1980
agtcccagca ctcagaaggc aaaagcaggc agatctctct aaatttgagg tcagcctagt    2040
ctacagagct gagttccagg acatgcaaga tacacagaaa aactgactgg aaaaaacaat    2100
aaccagagag agagagagag acagagacaa agacatacac acggagagaa acagagacag    2160
acacacacac acacacacac agagcgattg agctgacttc tgttacagag gacttaagtg    2220
gctaacaacc atctgtaact tcttttccag gggatctgat accctgttct gacctctgtg    2280
ggcgacaaat tcacatatga tatacatata tgtaggcaaa atactctgac ataccaaatt    2340
aatctaaaaa aatgtttata attttttaga aaaaagatc cgagtttctg agtcttatat    2400
ttttcatttg ccttccattt tttaaaataa tcttttttt ttattagatg aaatttattt    2460
ggttaacagt ccccagggct cactgaaaag attcataccc taatcccatg aatttgtaaa    2520
tattacctta tgttgttatg agaagaaatt taccctcaat caccccagca ggccttaagt    2580
acaattatat gcatctttat aaaagataaa agagttccca gcatgctaag aacagaatgt    2640
gaaacagcaa aggaatctca tgccataagc catcagaagc tagaaaagaa acacactctt    2700
tccaaagcat gtacaagaag ttcaagacta atacaaagtt ccagcctcta gaatcctctg    2760
cagtgtgctg ttatggaagc tacaagaagc taataagcac aggaaataaa cctttaaaga    2820
tcaataattg ggggcggtgg tgtatatata gtacagagaa tgttcttagc atgttcaaat    2880
ctctgggttc tgcctccacc acccaataaa gaaataatt gtgcttcaaa taacccaaag    2940
aatgtctaag acttttcct tggttttgtt ttggtttgtt tgtttgtttt tgagactcta    3000
tataggccag gcaggccttg aactcacata tctgattgcc tgttttcaa attccaggac    3060 taaaggtgtg tgacaccatg cccagcctga ctagttttg ttcttgtttt gagacagtgt    3120
ctcaccaagt agcccaaatt gatcccaaac tcaccatcca ccagcctatt tccatgattt    3180
ttaaacagtg ttttactata tagctctggc tgtcctgaaa cacactatat agaccaggct    3240
gacatcaacc tcaagagata tgtttccctt ttcttcctga gtgctgggag taaaggtata    3300
tgcctctatg cctaacttaa agggtttttt ttgagacaag gtctcactat gttgaccagg    3360
ttggcttccc tggctccaaa ttcaaagatc catctgcttc ttcctcacaa gtgtagtgtg    3420
ccctattgta taaacccctt catcccttat attaatcggt aaataaattt ttaaaatgta    3480
caagatacag ccaggtgcag tggcacatgt ctttaatcct agcacttggg aggcagaggc    3540
agtcgcagtc ggatttctct gaattccaga ccagacaggg ttacaaatgt aagacattgt    3600
ctcaaaatac aaacaaaaaa acaggataca atttgtccaa aataaacctg cagacctaag    3660
acaaactctt aagagggcta atatttacat atctaacaag aactatgtag gttttttccac    3720 aaacgggtgg agctcctgaa cagactaaac ataggcacag ttgtcactgt gggtgttctg    3780
```

```
ccagcacaag tgtaaagttg tcatcagaaa tgaatatgtg gcttcaagtg ccttacagaa      3840
tctaacaaac tcatagcttg tactatatac atgccaactc ttcgccaaat cacctaagtt      3900 cttttttaaaa tttctttaaa ttatatgtat ctgtgtgtat gtgcacatgc aggtacctaa     3960
ggaagccaat ggtattggag tttctaaagc tggagttatg ggttgttgtg agtcatctga      4020
cctgggtgct aaaaactgag ctcggatcct ttacaagagc agtaaatgcc tttaaatgct      4080
taactatctc ttgatgatga ttgttcaaag ttcatgaata acaatgtata aacaaactat      4140
atcaaatggt aactacattg ttttttaaact caatatagca tagcactggt ccaatctgga     4200
agaaggtaaa tgtatataaa aattatcaaa caaaaataaa agtgctgctg gtggctcatg      4260
actttgatcc tagcacttgg gaggcagagg caggcagatt tctgagttcg aggacagcca      4320
ggacagccag gactatacag agaaaccctg tctcaaaaaa acaaaacaaa acaaaacaaa      4380
aaaaaaagaa aagaaaaaag tgctcagcta cacagtggtg agctctgatc ccagcacgca      4440
ggaggaagag acaggccgat ttctgagttt gaggccagcc ttgtctacag agtaaattcc      4500
aggacaacca gggatataca gagaaaccct gtctcgaaaa aagaaaaaa agaaaacttc       4560 accctgtgtt ggctggatac caaacaaacc ttttccttt cttttttttt tttcttttt      4620 ttttggagac agggtttctc tgtgtagtcc tggctgtcct ggaactcact ctgtagacca     4680
ggctggcctt gaactcagaa atccgcctgc ctctgcctcc caagtgctgg gattaaaggc     4740
gtgtgccact acgccggctt ccctttttcta agtattgtc tcaagtattg cttagtacaa     4800
tcaatcccta acacttttt tgttaagtat cccttttcata aacattcaca aatcacttca     4860
gttgtttctt ctttccaact actactctgc ttattaacac ccacatacac atatagcttt     4920 attcttttt attttttat tttttttga cacagggttt ctctgtgtag tcctggctgt        4980
cctggaactc actctgtaga ctgagtgacc tcaaactcag aaatccgccg ccgccgccac     5040
caccaccacc cccagctta ttctttttttt agaaagggtc tctctacata gccctggcta    5100
tccttgaaat catgatgtag accaggctag cactgaactc agagatcctc ttgcctctgc     5160
aattaaaaac ccagttttag acaaactaaa taaaactgtg ttatttttc atttactaat     5220 cgctttaggt ttagttgcaa gaatgggcct ctaaccttaa acacaaagtg ctaaactttg     5280
atttgttttg tagacagggt ttcttttctgt agccctggct gtcctggaac tctgtagacc    5340
aggctggctt tgaactcaga atctgcctg cctctgcctc tgagtgctgg gatcaaaggc     5400
gtgcgccacc acgcccggca gtgctaaatg ttgaaaggc aaacattgtt agaatttta       5460 aaaaagattt atttatgtgt atggatattc tgtgcaccat gagggtgctg gatgctcttg     5520
gatcccctgg gactggagtt acagttgtgt actgacatgt aggtgttggg gattgaacct    5580
gagggattga gccagtgctc ttaaaacact tcactagcct cccagaattt tcaatgtgat    5640
agcctcaaaa tgtcagtgat tattagtaaa atgtccctac cacagagaaa tacttatcac    5700
acttattaac catcacattg gaaaagaaca tataagcagg aagtttattt cttcttcttc    5760
ttcttcttct tcttcttctt cttcttcttc ttcttcttct tcttcttctt ctttgggggg    5820
gggtgtattt caacatggga tttctcttgt acctccctgg ctgtcctgga actcactatg    5880
tagaccaggc taacctgaaa ctcagagatc tgcctgcctc tgtctcccaa gtgctgggat    5940
caaaggcatg tgctaacata gcctagacta agttttgttt tcttagcaca ttaaaccagg    6000
agtgcttatt tcagaccttt aaaacattag tggccaggcg tggtggtgta cgcctttaat    6060
tccagcactc agaggcagag gcaggcggat ttctgagttc aaggccagcc ttgtctacag    6120
agttccagga cagccagggc tatacagaga acccctgtct tgaaaaacca aaaacaaaaa    6180
```

```
actgactgta gatctgtaag tacctatgaa tttgatcaat gggaactgtc ctattttctc    6240
tcttttgtgt gtctgttgag ggaggggggtg gatttgagcc agactatcat aagagtgtgg    6300
aatggccctc aacttgctat gtagctgaga atggacttga ctggtcctct tcccattaca    6360
tccctactgc tgagattgca ggtcagcacc accatgccag gtttattccc tagtaaggga    6420
ctccaggcat ggtagaccag aattctacca accatacgta caaccttgaa attgacctga    6480
tttttaagaa aatgaataca ttacagatga gaactctgta cttcatatgc ttgtttggtg    6540 aaacattta ccaaacagac agataggctc aaagagtctg gtatggtggg gtcatacctg    6600
taacttcatc ccttgagaga ctgaggcagg aggaggattc tttcaaatca agaccaaact    6660
gggctacata atgagttcaa gataacatgg acaagagaga cctgttttta aaaacaaac    6720 aaacaaaaag acagtattta aaaaaaaag caaaacaaaa ctataaagag agctagagag    6780
atggctcagc acttaagggc actgactcct cttccagagg tcctgagttc aattcccagc    6840
aaccacatgg aggttcacag gtatctgtat cgggttctga tacacctcct ctggtgtgtc    6900
caaagacagg gacagtgtac tcacatatat aaaataaatc ttaaaacaaa caaacaacta    6960
ttaagagaca gaatctggcc gggcgtggtg gcacacacct ttagtcccag cactccggag    7020
gcagaggcaa aagtgagttc taggacagcc agggctacag agaaaccctg tctcgaaaaa    7080
ccaaaaaaaa aagagagaga gagagacaga atctgaaata ttccgaaaaa aaaaaaatga    7140
caacaccagg catggtgaca catgattttt aatcccaaca cctggaaggc agaggcaggg    7200
gtaatctcta tggatttgag gtcagcctaa cctgtagagc tagttgaagg acagccaagg    7260
cccatacaca gagaaacatt gtccaaaaaa ataaaaaaaa aaacccaaga atgtcaggat    7320
gggcctatat ctgctacaaa attaagaaca tctaagatag gctacatac ccagcccctt    7380 acttgccttt ttttaaaaaa caagtcacat acactgaaga tgtaatcagt cctattcatt    7440
tataagacag agtaggccct gctgacctga aactcacaaa gcatacaggt tggccataat    7500
cctatgttca ctctctaaga aatggtaaaa tttccctttt taacctcaag cccagaaac    7560 taatctatac cagaggaaaa acaggattaa tggtccattt attaaagagt actccaagac    7620
aaggtggtgg tggttgtggt ggtgggcggt catttcctcc atgctttgct aactgctaaa    7680
tgtctgaaaa tgataaaattc tagcattagc ccttttagag gaagactta ttattcattt    7740 ttacattttt ggtattgttt taaaactgaa acactggggg ggaagtatgg gggactttca    7800
gaatagcatt tgaaatgtaa atgaagaaaa tacctaataa aatttgaaa aaaaaaaaac    7860 aaaactgaaa cactgaaagg aaaggaagaa agcagagact gagcaagtgt ggctcacgcc    7920
tttaatcccg gcactctcga gaacaagcgg ctcgcggatc tctgagttca agactagcat    7980
ggtctacaga atgagggcta cacagagaaa ccatgtctgg aaggaaaaaa aaatattctg    8040
aaccatatct aggtagatgc cgtgagtcca ctatcacttt agagctcagt actgaagttg    8100
cactgttagt gtaaataagc agctaatggt tgtataatat gtttgtcctt tttaaagtgc    8160
cagtgactat ggaaatctct attcattaga aacatcacta aaacctgtca agcgccaggc    8220
ggtggtggta cacgccttta gtcccagcac ttgggaggca gaggcaggtg gatttctgag    8280
ttcgaggcca gcctggtcta caaagtgagt tccaggacac ccagagctat acttagaaac    8340
cctgtctcga aaacccaaa aaaaaaaaaa aaaacaaca acaacaaaaa aaaaaacctg    8400
tcaagcatga tagcaccaac aggtagatct cttcatgtga ggccagcctg agacataaaa    8460
cagaaaacta aattgaaatc atcagtccgt ccgtccccc cccccaccc cccgagacag    8520
```

-continued

| | | | | |
|---|---|---|---|---|
| ggtttctctg | tgtagccctg | gctgtcctgg | aactcacttt | gtagaccagg | ctggcctcaa | 8580 |
| actcagaaat | ccgcctgcct | ctgcctcccg | agtgctggga | tcaaagacgt | gcaccaccac | 8640 |
| cacccggcat | catcagtctt | ttgtaaaaag | tatgaaacta | tcttcttttc | tttctttct | 8700 |
| tcgtttttga | gacagggtct | gattatgctt | tggctgtcaa | gtaactcact | acatggacca | 8760 |
| ggaggctggc | ctcaaacaga | tatccatctt | cctgctagga | ttaaaggcaa | tgaccactaa | 8820 |
| cgccaggctg | gaattttctt | atcacaatga | ggtacctcta | cctcaaagac | tataaataaa | 8880 |
| tcaacagaca | cagataataa | atggaaatta | tacatttgtc | tagatactct | gagaagtgtg | 8940 |
| ggtattatca | acaccaacaa | aattgcagag | aaaatacaaa | aatatatgga | atcaaaacaa | 9000 |
| tgaataacaa | ctcaagatat | ggtggagtct | tctgtcccca | acaccctaaa | tacctcctaa | 9060 |
| atgaatcagc | ttttcaccc | cacaccagac | atcctcaaat | gaacagcaga | aataggagct | 9120 |
| tagagtatct | tgaatgttag | gggagaaaaa | tgttcttcgg | agaagagatt | cagataaaag | 9180 |
| aattgggaac | atgaatggtg | gtgacaagta | catgatgaca | caaacaaac | aaacaaaaaa | 9240 |
| ccaaatgtgt | ctattttat | taaggttttc | attatttcat | caatgacaat | tatccctcaa | 9300 |
| acatacaggc | cttggcccca | ctgtttccat | agaagcaaca | cgttttgact | tttgacatgt | 9360 |
| aactctcaaa | aactttcata | gagatagaaa | tacaaataca | gtgtccctgg | aaatgggtgc | 9420 |
| tagtggttaa | gtctattttt | cttggatgct | tttcattgca | agtactttac | ctaagtcatc | 9480 |
| tcattcaaaa | tttcaatatt | cttctcttaa | aagttttcaa | agactaaagg | cacgttctcc | 9540 |
| aaagtctcaa | gtgaagggag | gaacgtacca | aaaactacaa | gaaaatgat | taactcaagg | 9600 |
| gccacaagaa | aacatatgtt | ttccctaagg | taatatacag | aatgaatgcc | ttagttatag | 9660 |
| gagtcatttt | aagttaaaat | actcgccccc | acaaatgcaa | gagtaagctt | tattgggggg | 9720 |
| gggagggggg | aatcctgtct | ttctagtgac | tcctggcttg | ctctaagaat | ttaaccagcc | 9780 |
| aactcccgcg | ctccccacag | gagtccagcc | tctgcctctt | ggggaaggcc | ggccaatcgc | 9840 |
| gcgcttgggg | ctcattggct | cggagagacg | caactcaggc | gagaaaaacc | cgcctcccac | 9900 |
| attccgatgg | cccaaggacc | gatcggtagg | cagctatagg | aaaacccaat | tggcctatag | 9960 |
| gctcgccagt | caaatgcttc | ggcaaggcag | cttcacagaa | cctgcaagga | taaacatcc | 10020 |
| cgccccagtt | gtcctattgg | ctggcccgac | ccgtcgcggc | cccttcactg | tcgtcgtcca | 10080 |
| cccccccccc | caccagttca | gcggtccatt | catttcgtac | aataaccggt | gcaatggag | 10140 |
| cgggttcaag | atctcgtacg | ggtagacgag | actctgccac | ttacccaaga | tctaaagtga | 10200 |
| tcactcacgc | taaggcctgc | acggttcctc | tgtggtaaag | cggcaccaca | agccaccgct | 10260 |
| accgccgcct | tctgcgcaat | gccaaccgcc | cgccaaaacg | gatccttccc | tgcgcctgcg | 10320 |
| caaccaatcc | tgggcttgga | ccttttctcc | gcccaaaacg | cctgcgcaaa | actgacgct | 10380 |
| ggtcccgcca | ctacgcaggc | gcctaggttc | acaaccctct | cccgcccgcc | atttcacgtg | 10440 |
| ttccaggcag | caggcggaac | atcgtagtgc | gccggcgtga | actcgccatt | tttattacac | 10500 |
| atgcgcctta | tagggagtgg | ctgggaaaag | tcgcggtgag | ctactttgta | gcgtgcggtc | 10560 |
| ctttgacgag | tgagtttgta | atgttcgggt | gtgggaaagt | tatgaaaggc | atttaaaaga | 10620 |
| cgtgaataca | ttcaaatata | agtgactggc | tagttagcca | atcaatgcga | ttaaggataa | 10680 |
| gatcccttgg | ggcatcagtg | actcaaaggg | gcggagtctg | aatagaacgc | ccaaacggat | 10740 |
| gccgtttctt | agcagggcgt | cttcacgggc | caatggtggg | agggaataat | ttcaaatctc | 10800 |
| caataagact | caagtaaggg | cggagtctac | caataccgag | agcgaggagg | cgggataaaa | 10860 |
| gggcgagcag | aaggtaggct | ggcgggcacg | ttcgttatcg | tattcctttc | tgctctttga | 10920 |

```
cgctgccgag gaagcatcgc tgaaggctct cgtaactcta ccgtcatgtc taagtccgag    10980
gtaagttgga tgcgctttgc agcttctctt tcttccacac ttactgaata tagcgggatg    11040
tgacgtgttt tgctgctcgc acccgtggtt tcggtgtttt atcgattagt gctgaggcct    11100
actttaaaaa aatgcaggtc gccattttgt cctcatagtc accatgaggc tgcgatccga    11160
ccgccattaa cgtccatgca ctgttccttg tggcaaactt cacagactaa tgatctgggg    11220
agtgtggcct tttcttcccc tcccccattc tggtctaaca atcgcttgtt aaagagatat    11280
taagtcttaa tggggatgga cccgactaac ctgtgccctt tgttgcgcgt gcgtatgaag    11340
taaaagtaag gacgcatgcg ctgcgtgcaa ctcgagtgaa tccccagcag cacctcctag    11400
cctaggaagg agcacgtggt ctcgtgcagt aataaagaac aataaaaaag tgtagcatgt    11460
gttgttgcgg ggtgttgatt cattttccca ggttccagcc cctccgctaa acactccctc    11520
ctccacttta gtctcccaag gagccagaac agctgcggaa gctcttcatc ggagggctga    11580
gcttcgaaac aaccgacgag agtctgagga gccattttga gcaatgggga acactaacag    11640
actgtgtggt aagattaaaa gaaacaaaag gaagagctgg cttatttctt ccgatttaat    11700
ctgctgcttc ttagctaaat tgttttgtga agttaactaa tgggatggta aaaaaaaatc    11760
tggggctttc ttcagatctg taagaagctt acatttccac cccccactc tgaagtttca     11820 tgtttgcctt gatcagacta ggaatggctt ttgattctga gatcaggcag tgtattgatt    11880
gaattaactc taaacaggta atgagagatc caaacaccaa gagatccagg ggctttgggt    11940
ttgtcacata tgccactgtg gaagaagtgg atgctgccat gaatgcaaga ccacacaagg    12000
tggatggaag agttgtggaa cctaagagag ctgtctcaag agaagtgagt ggttttctc     12060 tttaacctga gactatgatt ggggcagtcc tcaattggga gatcccccc aagtggtatt     12120 aaaggcgagg gcctggaggt ggtggcacac gcctttaatc ccagcactcc ggaggcagag    12180
gcaggtatat ttctgagttc gaggctagcc tggtctacag agtgagttcc aggacagcca    12240
gggatatata gagaaaccct gtctctgaaa aaaggggggg ggtgggccac cacaccttcc    12300
cagtcattta gaaactgcta ctactaaata actgaagtca ttttccttt ttaggattct     12360 cagcgaccag gtgcccactt aactgtgaaa aagatctttg ttggtggtat taagaagac     12420 actgaagaac atcacctacg agattatttt gagcagtatg ggaagattga agtgatagaa    12480
attatgactg acagaggcag tgggaaaaag aggggctttg ctttttgttac ctttgatgac    12540 catgactctg tggataagat tgttagtaag tatcagagga ctacgtgttc cttaatgact    12600
ctggagtcct cttgtgtttt tttttttac agtcctgaat ctaccttttt ctcttagttc     12660
agaaatacca tactgtgaat ggccacaact gtgaagtaag aaaggctctg tcgaagcaag    12720
agatggctag tgcttcatcc agtcagagag gtgcgttaat ttttggttag attgtgggcg    12780
ccagcatgaa ttactatggg ttagcctaat gatccaaaaa tctcttttaa ggtcgcagtg    12840
gttctggaaa ctttggtggt ggtcgtgag gcggttttgg tggcaatgac aattttggtc      12900
gaggagggaa cttcagtggt cgtggtgtgt atggtttatt tttgattcct tgttggtttc    12960
agagctttta aatattaact gctaccctgt gtttccagca tttatggatt ttacccgaat    13020
atagttctag tacagaatta gattttgata agcattcatg tataaagcct ggtttaaagc    13080
tttggtttct tccaggtggc tttggtggca gccgtggtgg tggtggatat ggtggcagtg    13140
gggatggcta taatgaattt ggcaatgatg gtaagtttcc taaggagtct gtaagtaatg    13200
gtttctggaa acctgtacct ttagagtagg ctagtagaaa ctaaacttag tgcatgacaa    13260
```

```
agttcgatca gtcccataaa tgtgcatgct atgagcagcc tttagctatt atcttgcata    13320
cattttccct gttaaatact tttgtcttat tgagaagact tgtattctta taggtggtta    13380
tggaggaggc agccctggtt actctggagg aagcagaggc tatggaagtg gtggacaggg    13440
ttatggaaac cagggcagtg gctatggcgg gagtggcagc tatgacagct ataacaacgg    13500
aggaggcgga ggcggctttg cggtggtag tggtaggtat ccagtgatgc aggtacttgg    13560
cttggagcta gattagactt ctagagttta ttatgcccgt gttggacttt aaagctctta    13620
aagcattgtg ggtgcagtgc atggtgcgtt acagtaggcc tgctctgctg tgctacctcc    13680
tcctggcttt aagctgggc cgcctccccc aaaataagta ggtgaatgag tggttagtgt     13740
tgtcttcaat gtgagatagt tagatccaca ctacagttgg attgaatgtc taaactctgt    13800
tgggacttca ggcatttagt tgatacatcc aagaaatgta tgtattgacc tggaatacat    13860
aaaggccttc aattctaact tgccactgag aaacttaagt tgggttgatt ttactttaaa    13920
tgctggatta ttaactgaat gcctcactca gagaatgaag ccgaagggtt tggagttgac    13980
agaaggtcta taaatatcat aatctttgat tcagaccta agcactattg gcttgtcagt     14040
cctcaaagtc atcaatagag ctttttcctt ttctaggaag caattttgga ggtggtggaa    14100
gctacaatga ttttggcaat tacaacaatc agtcttccaa ttttgggccg atgaaggag     14160
gaaactttgg aggcaggagc tctggccctt atggtggtgg aggccagtac tttgctaaac    14220
cacggaacca aggtatagta tctatgacaa aagactgata gttaaatctc ccttcaaagg    14280
acatcaacta agagggtcat ataatcctta tttaggtcat cttaatttag gccagggact    14340
ttttttaaca gaaccattga tactacgttg cacaaagta ttaaaacaaa acattgtctt     14400
aattctacag gtggctatgg cggttccagc agcagcagta gctatggcag tggcaggagg    14460
ttctaattac atacagccag gtaagtgcct cctttgtgtg tgtttgctaa atgttataat    14520
tgaacccagt aacccaaatg tagctgagca gtacaacata gttaacatta taatttcagt    14580
aaaatggtgg atgttaagtt aatatgcagt tcagcaaaat ttgtgggaaa caacttgctc    14640
tattggattg tagccttgag tcttaatgtg ttttagatta acaactttat tccatattgt    14700
tcaacaggaa acaaagctta gcaggagagg agagccagag aagtgacagg gaagctacag    14760
gttacaacag atttgtgaac tcagccaagc acagtggtgg cagggcctag ctgctacaaa    14820
gaagacatgt tttagacaat actcatgtgt gtgggcaaaa actccaggac tgtatttgtg    14880
actaattgta taacaggtta ttttagtttc tgttctgtgg aaagtgtaaa gcattccaac    14940
aaaaggtttt actgtagacc ttttcacccc atgctgttga ttgctaaatg taatagtctg    15000
atcatgacgc tgaataaatg tgtctttttt ttttttttt taaatgtgct gtgtaaagtt    15060
agtctattct gaagccatct tggtaaactt ccccaacagt gtgaagttag aattccttca    15120
gggtggtgcc aagttccatt tggaatttat ttatggttgc ttgggtggag aagccattgt    15180
cttcaaaaac cttgatgtcg ttaaactgcc agttactatt gtaaccttta atgagtttca    15240
ccattgaaag ggtcatccaa gcaaggtcac aatttggtta taaatggtt gttggcacac    15300
cctatgcaat atcaaaattg aataacggta tcagataaaa taacagatgg gaatgaagct    15360
tatgtatcca ttatcatgtg tactcaataa acgatttaat tctcttgaat ggaatgacaa    15420
ctgtatggat ttgggactgg cagagatttg gactttccct acccaatgcc cctggtaaat    15480
gctcattgtt tgttaccaca gtgcaagttc aaagctctgc cagcagagag gccaactgct    15540
ggttaatgcc acctataagt ccagagatta gcattgttgg ggcatcttaa ctgataatta    15600
gtaagaactc ttaattgccc taacccatag gctgtagtga aggaaaactg cagtttaact    15660
```

```
gggttgtggg tgggtgttgc tttttggggtt ttgtcttttt ttttttttaat tttagatgat   15720 tctagttcat tggaattttta aattacaaat acagttaacc acgattatgt gtaattctgt   15780
attaacggca gttttccttc acactactgt cctcaagtgt taattgtata gaaaatgagt   15840
tcaaaacaat tactctccaa ttgttacttg tgcataggtt cttaaagagt ttcccatttg   15900
atgccccttt taagtgccat tgtaccgggt agcatagatg aatgtttacc acaggactat   15960
gtattccaac tcatgggtgt atatatattg cttggaagtt ttggtggagg ggggtgggag   16020
gagtgggagg tgagggtggg ggaagcatgg atggtagttc catgatactg gctgagtttg   16080
caatagcagg tggaacctta actattaagg gagtttgcag ataccctcagg aatcgggaca   16140 atgcctttaa agatccagga gatgttcagc tactaggaac tgctagcaag tatagcgcga   16200
atggcttcca gctcagaatc tctacagctg agagtagaca cttgtggtat gtggagtaca   16260
gataagccag gggcaggcca cggcacctcc atgaaagcta ggagggagtg aagtttgagt   16320
gaccatcgca aggaaggagg cagacgagag taaggcacac ctgactctta ggactagcag   16380
gcagagccag aaggaaaggt ttattgctat gctgctaggt aagaacagat tttacttaca   16440
tccatatagt tgtaaagtcc aattttctgt tggatttctt aattatattg agccaaaact   16500
agtccagtta agctgcactt ggttttttctg gagatgaatc gtttaaattt aatgccctat   16560
taatcttaaa ggaagtggat acatttctat ttgtgatgat acgttttggc ccttaaattt   16620
tatttaacct tcctttgacc cattttctta aaagtaatgg ctcaaagtaa tattagataa   16680
catttcccca aaatggtggg agggtgggtg ggttgctaat gggagggggt gggactagtt   16740
taatgatggg aattggcctc ataaaaggtt agttctaaat gttgtttgct tttctaggaa   16800
ggaatctgct atgaggctta actgctgtca taaaatttgt ttaaaaaatt ctgcagaagt   16860
tgctggccaa aaggtgagtt tttgtgacta cttcggtaag ctgtacatag aaaccaggag   16920
atgttaggga ggaatctaga tggagcccac cactgtctat gtgaaactgc atcactctct   16980
ctcttctcct ttacaggaac atccttaaga cagcagcctt tattctgggc cactgtactc   17040
cactcactgc catgcagttg ggttttagct gtactgctaa aaaatcattc aattttgtga   17100
atggcttact ttggtttttt tttttaaata aacttttttaa ttaactcctg tttcttgtct   17160
tcctttgtga cttagcaaca ttgagttaga atccacatta aaatctataa acagcctggt   17220
catggtggca aacacctcca gtcccaacac ttggaaaccc aagcatctac tttccttgga   17280
gttaggggtg ggatctgtat agttttcacc tggagaattt tacctctagc ttgttcttta   17340
ctgcctccat ctttaaaaga aactgatagc ccaaactttg agacccaagt gatgaaggac   17400
acaaagacct ttgcctgttt ttttctttct tgaggttaga aagggtttca cagtttaacc   17460
tggctgtcct gtctggaatt gaaggtgttc acccagcctt tttttttttt caaatatggt   17520
cttgctatgt gatcttgact ggcctaaaat ctccctgcct gtacatattt caaagtaaac   17580
ggaacgataa ggcagatttt tggttttttt caagactttc tctgtatagc cctggcctgt   17640
aactctttta gaccaggctg gcctcgaacc cagaaatccg cctgcctctg cctcccaggt   17700
gctggaatta aaggtatgcg ccgccatcac cacctggctg ataaggtata ttttgagttg   17760
ggtgtgccac acagcatccc aatacttgat aggaagattg gaagataagg tcattttcca   17820
gtatacaagt aggtggccag cttggattaa tgttggtgag tattccagta cccagttagc   17880
ttcaaggaga cacctgatct ccaggctcct tcatgaatat agtacattta gtcacatact   17940 caaaattttat agagaggttg gattgtggca caacatacct ttcatcccag cactttggag   18000
acgggcaatg gatttttttat gagttggaag ctaacttact tggtccatcc tgtcacaaag   18060
```

```
gtaagtctaa cgccaggcgt ggtgggacat gcctttaatc ccagcacttg gcaggcagag    18120
gcaggtgaat ttctgagttt gaggccagtc tggtctgcag agtgagttac aggacaacca    18180
gggctacaca gagaaaccct gtctcaaact aaaaaaaaag tacatctaaa aagagtagaa    18240
ttgatagcat cccccaagca caagggctgg tttgtggcct cttgggttga gactaggtgc    18300
aatgcagagc tgaatatgtg aatatggagc atcactaagg tgtaggtgta aaatgctttt    18360
aaatttagtg cctattcaaa ctcattccag aaggatctgg cctctcagat gcaaagtgag    18420
aaacaggaga atatcaggtg gatgctccag agaccttcca tagaggatac agccaacttt    18480
ggtagctctt ggtgtttagg aatgggggc agagggagtg gggagtcacc aatgaactga     18540
aggcacattg ctcatgccca aattttatat atgctctaag tgagcttagg attttttcc     18600 ttcaatataa actgatttct gagataattt ggcttcctaa ccctcaaaga agacacaata    18660
gaaagctatt tccacacagc tctttatgaa ccaaagcttg gacaagaggt ggggttgagg    18720
acctgagaag ccaacacctg gcctccaggc aaacctcacc aaatactccc aggtgatatg    18780
gttacatctg ccttttggtc tggaggactc tgagtcttgt gggattaaga agtgccttca    18840
tcagaaggga atgagggagt ctctagcacc agtgtccact ctctagacca gctcaatctg    18900
tagcctccat tttggttcca cggggtacca gaaagatggc accatcagca gcctgttgca    18960
gtacatattc ctctggtgag taactgttgc cagattcatc ccgaagatgc tggaaaatat    19020
catggtacag ctctgccagc tgttggcgca tgacctccag agtgcggtca gcctcccctc    19080
gggctctgag aagccgctcc ctttcactgc tcagccgctc cagctctcgc tccagctgca    19140
caatggtttc cagttttctc ttgcgacagt tttgggctgc caccttgttc ttgccccgtc    19200
gacggatgtc ccgaactaga gccagctggc tctccgttag cggatactgt gccaacaact    19260
cattaaagtc atctaccggc aagttaacta tcttgtccgt agggaaagga atcttcatgg    19320
ccagggctcg ccgctcgtcc cgactccctg cctccccacg gacagcaggc ttagcccgaa    19380
ctggaccgga ggatgactct aaggccaagg gtgtctcagt gggtggaaga gtatagttgg    19440
gatgggccaa agaattgggc ataagtgagt aaggatactc cactgggtac atgtccgcgt    19500
actcgctcct ccgcctgcca gcctccatac cctctagctc aagagattct gcatcactgt    19560
agttgaggga taatcctgag tcagattctg ggtcttcttg gggcttgggt tgccccactg    19620
gcagcccaat gtccaggaga gctaagtggt ctggagggg ctcattgagc aggcctgaaa     19680
gggtaagtgg ctttgacact ggtatggcta cattaccata ggagtatggt agttctggga    19740 catgggagt agatgctggg agctcataag atggtggggg aagggagaag cctgcatctg     19800
gatgaattga acaggggcaa tatgttggag gtggcagtgg cccagggtat ggggtgggtg    19860
cttgaggctc aaaagatgtc tcacttggaa catttagacc ctgcaaagaa aaaataaag     19920 aggattaaga agatcgacta tgttgggcag tggtggtaaa cacctttaat cccagcatct    19980
aaaagacaaa tccaatctct gcgttctagg gtagcctgca ccataaagta aactccagga    20040
ctatatagag aaactctgtc tgggaaaagg aaagaaagaa actgggtatg gtggcacacc    20100
tttaatctca gtaccctgga tgcagaggca gccagatctc ggagttcaaa gccac         20155
```

<210> SEQ ID NO 3
<211> LENGTH: 34
<212> TYPE: DNA
<213> ORGANISM: Saccharomyces cerevisiae
<220> FEATURE:
<221> NAME/KEY: protein_bind
<222> LOCATION: (1)..(34)

<400> SEQUENCE: 3
gaagttccta ttctctagaa agtataggaa cttc    34

<210> SEQ ID NO 4
<211> LENGTH: 801
<212> TYPE: DNA
<213> ORGANISM: Streptomyces fradiae
<220> FEATURE:
<221> NAME/KEY: gene
<222> LOCATION: (1)..(801)

<400> SEQUENCE: 4

```
atgggatcgg ccattgaaca agatggattg cacgcaggtt ctccggccgc ttgggtggag    60
aggctattcg gctatgactg ggcacaacag acaatcggct gctctgatgc cgccgtgttc   120
cggctgtcag cgcaggggcg cccggttctt tttgtcaaga ccgacctgtc cggtgccctg   180
aatgaactgc aggacgaggc agcgcggcta tcgtggctgg ccacgacggg cgttccttgc   240
gcagctgtgc tcgacgttgt cactgaagcg ggaagggact ggctgctatt gggcgaagtg   300
ccggggcagg atctcctgtc atctcacctt gctcctgccg agaaagtatc catcatggct   360
gatgcaatgc ggcggctgca tacgcttgat ccggctacct gcccattcga ccaccaagcg   420
aaacatcgca tcgagcgagc acgtactcgg atggaagccg gtcttgtcga tcaggatgat   480
ctggacgaag agcatcaggg gctcgcgcca gccgaactgt tcgccaggct caaggcgcgc   540
atgcccgacg gcgatgatct cgtcgtgacc catggcgatg cctgcttgcc gaatatcatg   600
gtggaaaatg gccgcttttc tggattcatc gactgtggcc ggctgggtgt ggcggaccgc   660
tatcaggaca tagcgttggc tacccgtgat attgctgaag agcttggcgg cgaatgggct   720
gaccgcttcc tcgtgcttta cggtatcgcc gctcccgatt cgcagcgcat cgccttctat   780
cgccttcttg acgagttctt c                                             801
```

<210> SEQ ID NO 5
<211> LENGTH: 24
<212> TYPE: DNA
<213> ORGANISM: Artificial Sequence
<220> FEATURE:
<223> OTHER INFORMATION: A1U primer

<400> SEQUENCE: 5
tatagcggga tgtgacgtgt tttg    24

<210> SEQ ID NO 6
<211> LENGTH: 24
<212> TYPE: DNA
<213> ORGANISM: Artificial Sequence
<220> FEATURE:
<223> OTHER INFORMATION: WT-L primer

<400> SEQUENCE: 6
aatgaatcaa cacccgcaa caac    24

<210> SEQ ID NO 7
<211> LENGTH: 24
<212> TYPE: DNA
<213> ORGANISM: Artificial Sequence
<220> FEATURE:
<223> OTHER INFORMATION: KO-L primer

<400> SEQUENCE: 7
actgcaccca caatgcttta agag    24

HNRNP A1 KNOCKOUT ANIMAL MODEL AND USE THEREOF

CROSS-REFERENCE TO RELATED APPLICATIONS

This application is a Continuation-in-part of the pending U.S. patent application Ser. No. 13/600,635 filed on Sep. 14, 2011, for which priority is claimed and is incorporated herein by reference in its entirety.

Although incorporated by reference in its entirety, no arguments or disclaimers made in the parent application apply to this divisional application. Any disclaimer that may have occurred during the prosecution of the above-referenced application(s) is hereby expressly rescinded. Consequently, the Patent Office is asked to review the new set of claims in view of the prior art of record and any search that the Office deems appropriate.

BACKGROUND

1. Technical Field

The present disclosure relates to vectors comprising Heterogeneous nuclear ribonucleoprotein (hnRNP) A1 gene and non-human animals in which the expression of hnRNP A1 gene has been disrupted.

2. Description of Related Art

Heterogeneous nuclear ribonucleoprotein (hnRNP) A1 is a protein that has been reported to play a significant part in regulating the process of gene splicing (Del Gatto-Konczak et al., 1999 MOI Cell Biol 19, 251-260), telomere extension (LaBranche et al., 1998 Nat Genet 19, 199-202), and viral replication (Lin et al., 2009 J Virol 83, 6106-6114; Monette et al., 2009, J Biol Chem 284, 31350-31362), and any of the identified cellular events has been implicated with diseases including cancerous progression carcinogenesis, and neurodegenerative disease.

Recently, hnRNP A1 is identified to be involved in alternative splicing of many disease-related proteins, such as GTPase Rac1 and carcinoembryonic antigen-related cell adhesion molecule-1 (CEACAM1). Rac1b, an alternatively spliced isoform of Rac1, was originally identified as an over-expressed protein in breast and colorectal cancer cells, and has subsequently been suggested an important role in many oncogenic signaling pathways. CEACAM1 is expressed in a variety of cell types, including breast cancer cells, and is also implicated in carcinogenesis. Alternative splicing of Exon 11 of the insulin receptor gene (INSR), which is developmental stage-dependent and tissue-specific, is also regulated by hnRNP A1. hnRNP A1 inhibits exon 11 inclusion and results in insulin receptor-B (IR-B) expression, which predominantly express in insulin-sensitive tissue, suggesting a metabolic role (Talukdar et al., *PLoS One* (2011), 6: e27869). It is demonstrated that hnRNP A1 is a negative factor to splicing selection of Ataxia Teleangectasia Mutated gene (ATM), the gene mutated in an autosomal recessive disorder characterized by cerebellar ataxia and oculocutaneous telangiectasias (Pastor et al., *PLoS One* (2011), 6: e23349).

In view of the role of hnRNP A1 associated with various diseases, it is useful to provide an animal model, particularly, a hnRNP A1 knockout model, in which the expression level of hnRNP A1 protein is not expressed in null mice and the expression level of hnRNP A1 in the heterozygous in the knockout model is relatively low, as compared to a normal animal, for further studies on the function of hnRNP A1 gene in any of the identified diseases and its use in developing therapies to treat any of these diseases.

SUMMARY

As embodied and broadly described herein, disclosure herein features vectors comprising hnRNP A1 gene and non-human animals and cell lines in which the expression of hnRNP A1 gene has been disrupted.

Accordingly, in one aspect, the present disclosure is directed to a targeting vector or a nucleic acid construct, which includes a nucleic acid sequence, in which a first locus of recombination sequence 1 is inserted before the exon 2 of the endogeneous hnRNP A1 gene, and second recombination sequences 2 flanking a marker gene followed by a second locus of recombination sequence 1 is inserted behind the exon 8 of the endogenous hnRNP A1 gene.

In another aspect, the present disclosure is directed to a cell containing the nucleic acid construct of the present invention or a disrupted hnRNP A1 gene. Preferably, the cell is a stem cell, and more preferably, an embryonic stem (ES) cell, and most preferably, a murine ES cell. According to one embodiment, the cell is produced by introducing the nucleic acid construct of the present invention into a stem cell to produce a homologous recombinant, resulting in a disruption in the hnRNP A1 gene, in which the neomycin resistant gene and the exons 2 to 8 of the hnRNP A1 gene are respectively deleted by the introduction of FLP recombinase and Cre recombinase.

In still another aspect, the present disclosure provides a non-human animal and its progeny having a disruption in hnRNP A1 gene. In one embodiment, the non-human animal and its progeny are heterozygous or homozygous for a null mutation in the hnRNP A1 gene. In another embodiment, the non-human animal and its progeny having a disruption in hnRNP A1 gene exhibit decreased expressed levels of the hnRNP A1 gene, relative to the wild-type non-human animals. Preferably, the non-human animal and its progeny are rodents and, most preferably, are mice.

In a further aspect, the present disclosure provides a method of obtaining a non-human animal deficient in hnRNP A1 gene, or with decreased or null expressed level of hnRNP A1 gene. The method includes steps of inserting into the genome of the embryonic stem cell derived from the non-human animal the nucleic acid construct of the present invention, injecting the embryonic stem cell into a blastocyst of the non-human animal after introduction of appropriate recombinase, and implanting the blastocyst into the uterus of a foster mother. Preferably, the non-human animal is rodent and, most preferably, is mouse.

The non-human animals of the present disclosure are useful for studying hnRNP A1 gene and diseases wherein hnRNP A1 gene is implicated, including neurodegenerative disease and cancer. The non-human animals of the present disclosure are useful for identifying therapeutic compounds that may be useful in preventing and/or treating any of these diseases.

Accordingly, in still a further aspect, the present disclosure provides a method of screening a compound for potential use in modulating the function of the hnRNP A1 gene that linked to the prevention and/or treatment of neurodegenerative disease or cancer. The method includes steps of respectively administering a test compound to the non-human animal deficient in hnRNP A1 gene and a wild-type non-human animal or cells or tissues derived thereof; and assessing the function of exonic RNA splicing in each of the non-human animal, cells, or tissues defined above, prior to and after a given time period of the administration; and comparing the non-human animal deficient in hnRNP A1 gene with the wild-type non-human animal in terms of the test results to determine effectiveness of the test compound. Preferably, the non-human animal is rodent and, most preferably, is mouse.

In a further aspect, the present invention further relates to a transgenic knockout mouse the genome of which is manipulated to comprise a homozygous disruption of hnRNP A1 gene, wherein the mouse exhibits muscle abnormalities characteristic of developmental disorder and muscular diseases as compared to a wild type mouse in which the hnRNP A1 gene is not disrupted.

The details of one or more embodiments of the invention are set forth in the description below. Other features, objects, and advantages of the present invention will be apparent from the description, and from the claims.

BRIEF DESCRIPTION OF THE DRAWINGS

The patent or application file contains at least one drawing executed in color. Copies of this patent or patent application publication with color drawing(s) will be provided by the Office upon request and payment of the necessary fee.

The present description will be better understood from the following detailed description read in light of the accompanying drawings.

DETAILED DESCRIPTION

Figure 1:
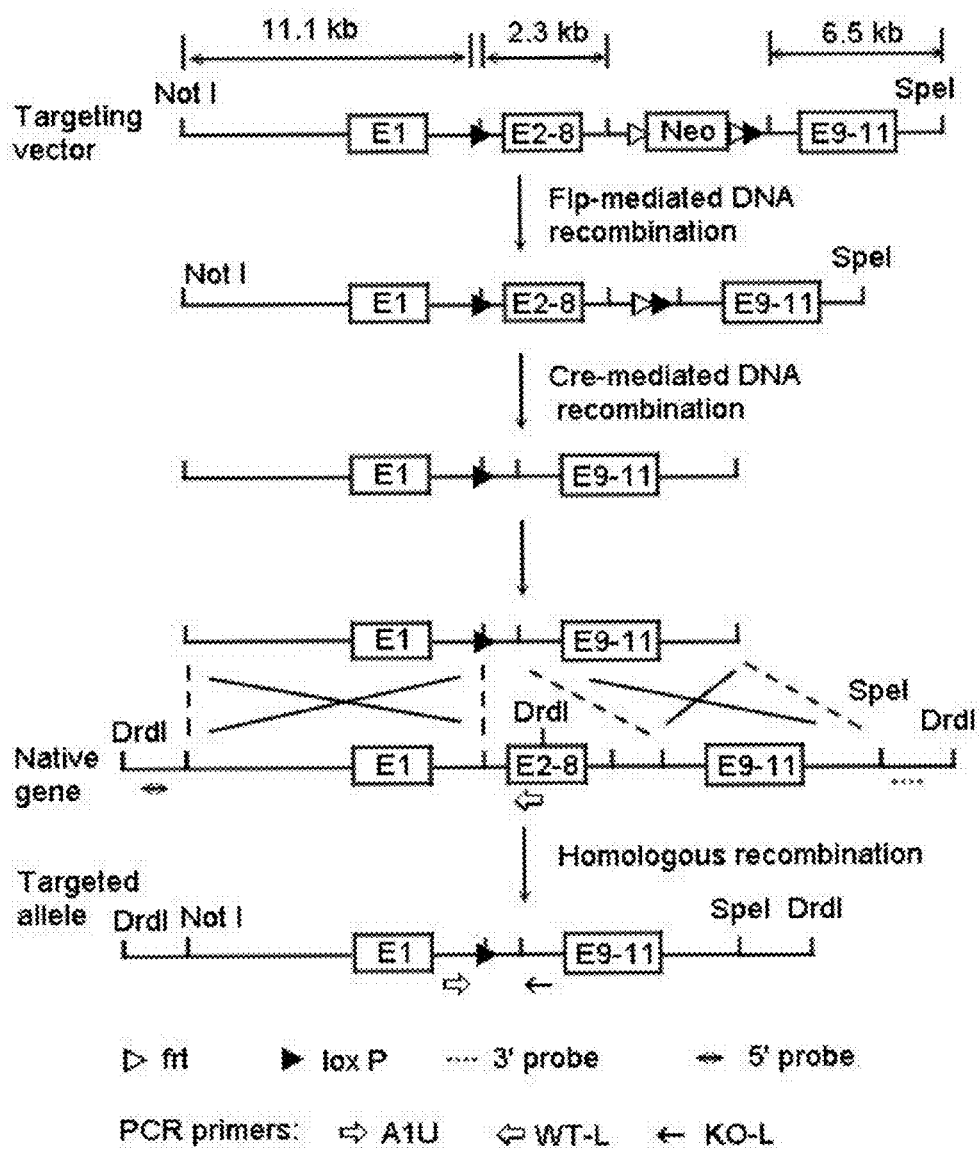
FIG. 1 is a schematic drawing illustrating the construction strategy of a nucleic acid construct having DNA fragments with exons 2 to 8 of hnRNP A1 being deleted for generating hnRNP A1 knockout mice in accordance with one embodiment of this invention.

The detailed description provided below in connection with the appended drawings is intended as a description of the present examples and is not intended to represent the only forms in which the present example is constructed or utilized. The description sets forth the functions of the examples and the sequence of steps for constructing and operating the examples. However, the same or equivalent functions and sequences may be accomplished by different examples.

1. Definitions

The terms "a", "an", and "the" as used herein are defined to mean "one or more" and include plural referents unless the context clearly dictates otherwise.

The term "gene" refers to a gene containing at least one of the DNA sequence disclosed herein, or any DNA sequence encodes the amino acid sequence encoded by the DNA sequence disclosed herein, or any DNA sequence that hybridizes to the complement of the coding sequence disclosed herein. Preferably, the term includes coding and non-coding regions, and preferably all sequences necessary for normal gene expression including promoters, enhancers, and other regulatory sequences.

The term "nucleic acid" refers to polymeric forms of nucleotides of any length. The nucleic acid may contain deoxyribonucleotides, ribonucleotides, and/or their analogs. Nucleotides may have any three-dimension structure, and may perform any function, known or unknown. The term "nucleic acid" includes single-, double-stranded and triple helical molecules. Non-limited examples of nucleic acids include, but are not limited to, a gene or its fragment, exons, introns, mRNA, tRNA, rRNA, ribozymes, cDNA, recombinant nucleic acid, plasmids, vectors, isolated DNA or RNA of any sequence, nucleic acid probes and primers. A nucleic acid may also comprise modified nucleic acid molecules, such as methylated nucleic acid molecules and nucleic acid analogs.

The term "homologous recombination" refers to exchange DNA fragments between two DNA molecules at the site of homologous nucleotide sequence.

The term "homologous" are used herein to denote a characteristic of a DNA sequence having at least 70% sequence identity as compared to a reference sequence, typically at least about 85% sequence identity, preferably at least about 95% sequence identity, and more preferably about 98% sequence identity, and most preferably about 100% sequence identity as compared to a reference sequence. Homology can be determined using, for example, a "BLASTN" algorithm. It is understood that homologous sequence may accommodate insertions, deletions, and substitutions in the nucleotide sequence. Thus, linear sequence of nucleotides can be essentially identical even if some of the nucleotides residues do not precisely correspond or align. The reference sequence may be a subset of a large sequence, such as a portion of a gene or flanking sequence.

"Disruption" of an hnRNP A1 gene occurs when a fragment of genomic DNA locates and recombines with an endogenous homologous sequence. These sequence disruptions or modifications may include insertions, missense, framshift, deletion, substitutions, or replacement of DNA sequence, or any combinations thereof. Insertions include the insertion of the entire genes, which may be of any origin. Disruption, for example, can alter or replace a promoter, an enhancer or splice site of the hnRNP A1 gene, and can alter the normal gene product by inhibiting its production partially, or completely. In a preferred embodiment, the disruption is a null disruption, wherein there is no significant expression of the hnRNP A1 gene.

The practices of this invention are hereinafter described in detail with respect to targeting vectors or nucleic acid constructs comprising a nucleic acid sequence comprising hnRNP A1 gene; and non-human animals in which the expression of hnRNP A1 gene has been disrupted. Among other uses and applications, the animal model developed in this invention are useful in various screening assays for the identification of therapeutically useful compounds for the treatment of diseases and/or conditions involving the expression of hnRNP A1 gene.

2. Generation of the Targeting Vector or Nucleic Acid Construct

In order to prepare a knockout animal, a targeting vector or nucleic acid construct containing hnRNP A1 gene is constructed. The nucleic acid construct is designed to disrupt the expression of hnRNP A1 gene in a cell. The general features of the nucleic acid construct are that it contains a nucleic acid sequence from one or more regions of the hnRNP A1 gene.

Accordingly, in one aspect, the present disclosure provides a vector or a nucleic acid construct, which includes a genetic engineer heterogeneous nuclear ribonucleoprotein (hnRNP) A1 gene, wherein a first locus of recombination sequence 1 is inserted before exon 2 of the hnRNP A1 gene, and recombination sequences 2 (i.e. a first locus and a second locus of the recombination sequences 2) flanking a marker gene followed by a second locus of recombination sequence 1 are inserted behind exon 8 of the hnRNP A1 gene. The recombination sequence 1 at the first locus undergoes recombination with the recombination sequence 1 at the other locus in the presence of its corresponding recombinase. Similarly, the recombination sequence 2 at the first locus undergoes recombination with the recombination sequence 2 at the other locus in the presence of its corresponding recombinase. Of note is that, the recombination sequence 1 and the recombination sequence 2 belong to different recombination sequence/recombinase system. In one embodiment, the recombination sequence 1 and its corresponding recombinase belong to Cre/loxP system, and the recombination sequence 2 and its corresponding recombinase belong to FLP/frt (FLP recombination target) system. More specifically, the hnRNP A1 gene is disrupted by introduction of Cre recombinase and FLP recombinase.

The Cre/loxP system is a well known system for artificially control gene expression (Kuhn and Torres, 2002 Methods Mol Biol 180: 175-204). The system begins with the cre gene, which encodes a site-specific DNA recombinase named Cre or cyclic recombinase. A site-specific DNA recombinase means that the Cre protein recombines DNA when it locates specific sites in a DNA molecule. These sites are known as loxP or locus of crossover (x) in P1 sequences (SEQ ID NO: 1). When cells that have loxP sites in their genome also express Cre, the protein may catalyze a reciprocal recombination event between the loxP sites, which means the double stranded DNA is cut at both loxP sites by the Cre protein and then ligated back together. As a result, the DNA between the loxP sites is excised as a circular DNA and subsequently degraded. In order to prepare the nucleic acid construct, the genomic DNA sequence of hnRNP A1 gene (SEQ ID NO: 2) is digested with restriction enzymes and the loxP sites are ligated into the genomic DNA sequence at desired locations using methods known to those skill artisans or as described in Examples of this application. The FLP/frt system is functionally analogous to the Cre/loxP system. Further examples of recombinases include, but are not limited to, lambda Int protein, IHF, Xis, Hin, Gin, Cin, Th3 resolvase, TndX and XerD. As to recombination sequences (sites), examples include, but are not limited to, loxP site, frt site (SEQ ID NO: 3), att site, six sites, res sites, rox sites, psi sites and cer site (see WO2001/1042590).

A marker gene used for selection may be included in the nucleic acid construct, so as to identify cells that have been successfully transfected with the nucleic acid construct of the present invention. The marker gene can be any marker that can be used to detect the presence of the nucleic acid in a cell. Preferred marker genes are antibiotic resistance genes such as neomycin-resistant gene (Neo, SEQ ID NO: 4), the reporter lacZ gene and the herpes simplex virus thymidine kinase gene (HSV-tk). In one embodiment, the marker sequence is a neomycin-resistant gene. The marker gene may be inserted with recombination sequences flanking each end of it.

In a preferred embodiment of the present invention, the nucleic acid construct is generated by first amplifying sequence homologous to the target sequence (such as the hnRNP A1 gene) and then inserting the loxP sequences, and a neomycin resistant gene in combination with frt sequences at each end into the amplified product so that it is flanked by the homologous sequence. Specifically, a loxP sequence is inserted before the exon 2 of the endogeneous hnRNP A1 gene, and FLP recombinase target (frt) sequences flanking a neomycin-resistant gene followed by another loxP sequence is inserted behind the exon 8 of the endogenous hnRNP A1 gene. More specifically, the first locus of loxP sequence is inserted between the exon 1 and exon 2 of the endogeneous hnRNP A1 gene, and the neomycin-resistant gene flanked by frt sequences and the second locus of loxP sequence are inserted between exon 8 and exon 9. Preferably, the nucleic acid construct is as depicted in FIG. 1.

The nucleic acid construct containing the hnRNP A1 gene, the Cre/lox system and the marker gene can be inserted directly into appropriate host cells such as embryonic stem cells as will be described below or it may be placed in suitable vectors for amplification prior to insertion.

3. Generation of the Transfected Embryonic Stem Cells

The above nucleic acid constructs or vectors may be transfected into an appropriate host cell using any method known in the art. Various techniques may be employed for such purpose, which include and are not limited to, microinjection of DNA into the nucleus, retrovirus mediated gene transfer into germ lines, electroporation of embryos, sperm-mediated gene transfer, and calcium phosphate/DNA co-precipitates, transfection or the like.

In a preferred embodiment, the nucleic acid construct is transfected into host cells by electroporation. In this process, electrical impulses of high field strength reversibly permeabilize biomembranes allowing the transfection of the nucleic acid construct. The pores created during electroporation permit the uptake of macromolecules such as DNA into the host cells.

Any cell type capable of homologous recombination may be used to practice this invention. Preferred cell types include embryonic stem (ES) cells, which are typically obtained from pre-implantation embryos cultured in vitro. The ES cells are cultured and prepared for transfection of the nucleic acid construct using methods known in the related art. The ES cells that will be transfected with the targeting vector or nucleic acid construce are derived from embryo or blastocyst of the same species as the developing embryo or blastocyst into which they are to be introduced. ES cells are typically selected for their ability to integrate into the inner cell mass and contribute to the germ line of an individual when introduced into the animal in an embryo at the blastocyst stage of development. In one embodiment, the ES cells are isolated from the mouse blastocysts, in another embodiment, from the 129/SvJ strain.

After transfection into the ES cells, the nucleic acid construct integrates with the genomic DNA of the cell in order to delet the transcription of the native hnRNP A1 gene. Preferably, the insertion occurs by homologous recombination wherein regions of the hnRNP A1 gene in the nucleic acid construct hybridize to the homologous hnRNP A1 sequence in the ES cell and recombine to incorporate the construct into the endogenous hnRNP A1 gene.

After transfection, the ES cells are cultured under suitable condition to detect transfected cells. For example, when the marker gene comprises an antibiotic resistant marker, the cells are cultured in that antibiotic. In one embodiment, the neomycin resistant gene is present, and the ES cells are exposed to neomycin analog, G418. ES cells that express the introduced neomycin (Neo) resistant gene are resistant to the compound G418, whereas ES cells that do not carry the Neo gene marker cannot survive. The DNA and/or protein expression of the surviving ES cells may be analyzed using Southern Blot technology and/or Western Blot technology as described in the Examples of this application, in order to identify the ES cells with the proper integration of the construct. The neomycin resistant gene is then removed by the introduction of FLP recombinase; and the hnRNP A1 gene segment flanked by the two loxP sequencess, or more specifically the exons 2 to 8 of hnRNP A1 gene, of the survived ES cells may then be removed by the introduction of Cre recombinase.

4. Generation of the Knockout Animals

The selected ES cells are then injected into a blastocyst of a non-human animal to form chimeras. The non-human animal may be a mouse, a hamster, a rat or a rabbit. Preferably, the non-human animal is a mouse. In particular, the ES cells are inserted into an early embryo using microinjection. For microinjection, 10 to 20 ES cells are collected into a micropipette and injected into 3 to 5 day old bastocysts recovered from female mice. The injected blasocysts are re-implanted into a foster mother. When the pups are born, typically 18 to 20 days later, they are screened for the presence of nucleic acid construct of this invention. In one embodiment, DNA collected from the tail tissues of the pups may be screened using Southern Blot and/or PCR technique as described in Examples of this disclosure. The heterozygotes are identified and are then crossed with each other to generate homologous knockout animals.

Accordingly, the present invention provides a transgenic non-human animal and its progeny, whose genome comprising a disruption in hnRNP A1 gene, wherein the animal has a decreased (i.e., heterozygous disruption) or null (i.e., homozygous disruption) expression level of the hnRNP A1 gene as compared to that of a wild-type animal. The present invention also provides cells or tissues, including immortalized cell lines and primary cells or tissues, derived from the transgenic non-human animal and its progeny. The expression of the hnRNP A1 gene may be partially or completely disrupted. In the case when a complete disruption occurs, the level of hnRNP A1 gene is not detectable by Southern blotting. In one embodiment, the disruption affects at least two exons within the hnRNP A1 gene. In another embodiment, the exons are exons 2 to 8.

In one embodiment, the transgenic non-human animal and its progeny are mice, hamsters, rats or rabbits. In another embodiment, the transgenic non-human animal and its progeny are mice. The homozygous disruption in the hnRNP A1 gene of the transgenic mouse results in damaged function of exonic RNA splicing, a reduced weight relative to a wild-type control mouse at embryonic stage, and/or perinatal mortality. Furthermore, the transgenic mouse with heterozygous disruption in the hnRNP A1 gene is predisposed to premature aging diseases and/or virus infective diseases.

The present invention further provides a method of preparing transgenic non-human animal with decreased or null expression level of hnRNP A1 gene comprising steps of inserting into the genome of the embryonic stem cell derived from the non-human animal the nucleic acid construct of the present invention, injecting the embryonic stem cell into a blastocyst of the non-human animal after introduction of appropriate recombinases, and implanting the blastocyst into the uterus of a foster mother of the non-human animal. In one embodiment, the non-human animal is a mouse, a hamster, a rat or a rabbit. In another embodiment, the non-human animal is a mouse.

In a preferred embodiment, the method includes steps of: (1) obtaining a nucleic acid sequence containing a hnRNP A1 gene or a portion thereof; (2) preparing a nucleic acid construct of the present invention; (3) transfecting the nucleic acid construct into an ES cell; (4) selecting an ES cells that has integrated the nucleic acid construct into its genome; (5) introducing FLP and Cre recombinases to the selected ES cells in step (4) to remove the marker gene and exons 2 to 8 of the hnRNP A1 gene and generate a deleted hnRNP A1 gene; (6) introducing the selected ES cell in step (5) into a blastocyst to form a chimera blastocyst; (7) implanting the chimeric blastocyst into a pseudopregnant mother, wherein the mother gives birth to a chimeric animal having the disrupted hnRNP A1 gene in its genome; (8) crossing the chimeric animal obtained in step (7) with a normal animal to obtain a heterozygous knockout animal; (9) repeating the crossing defined in step (8) at least 1 time to generate another heterozygous knockout animal; and (10) crossing the heterozygous knockout animals obtained in step (8) and (9) with each other to generate a homozygous or heterozygous hnRNP A1 knockout animal. Preferably, the crossing step defined in step (8) is repeated at least 2, 3, 4 or 5 times to generate the heterozygous knockout animals. More preferably, the crossing step defined in step (8) is repeated at least 5 times to generate the heterozygous knockout animals.

In a preferred embodiment, the non-human heterozygous knockout animal is a heterozygous hnRNP A1 knockout mouse.

5. Use of the Knockout Animals

The knockout animals of the present invention are useful for studying the function of hnRNP A1 gene and diseases wherein the hnRNP A1 gene is implicated, including neurodegenerative disease and cancer. Hence, the non-human hnRNP A1 knockout animals of the present disclosure are useful for identifying therapeutic compounds that may be useful in preventing and/or treating any of these diseases.

Accordingly, the present disclosure provides a method of screening a compound for potential use in prevention and/or treatment of neurodegenerative disease or cancer. The method includes steps of respectively administering a test compound to a non-human animal comprises a disruption in hnRNP A1 gene or primary cells or tissues derived therefrom and a wild-type non-human animal or primary cells or tissues derived therefrom; and assessing functions of exonic RNA splicing in each of the non-human animal, cell, or tissue defined above, prior to and after a given time period of the administration; and comparing the assessment results to determine effectiveness of the test compound.

In one embodiment, the non-human animal is a mouse, a hamster, a rat or a rabbit. In another embodiment, the non-human animal is a mouse.

In a further embodiment, the primary cells or tissues derived from the hnRNP A1 gene-disrupted mouse are prepared by a method well known in the art (Kazutoshi et al., Nature Protocols (2007), 2: 3081-3089; and Yen et al., Environmental Health Perspectives (2010), 118: 949-956). The primary cells can be fibroblasts from the non-human animal embryos or myoblasts from the neonatal non-human animal. The the non-human animal may be, but not limited to, mouse. Briefly, the process for preparing mouse embryonic fibroblasts (MEF) includes the following steps: (1) isolating mouse embryos at day 13.5 and removing the head, visceral tissues and gonads from the islated embryos; (2) hashing out the remaining embryonic body and incubating in a solution containing trypsin and EDTA under 37° C.; (3) dissociating the embryonic body in appropriate medium to form a cell suspension; (4) centrifuging the cell suspension to enrich the MEFs; and (5) culturing the MEFs in appropriate medium with suitable cellular concentration. The primary myoblasts of can be prepared from the forelimb and hind limb of neonatal mouse through the following steps: (1) removing surrounding connective tissue and mincing the muscles into small pieces; (2) digesting the minced muscles with collagenase; (3) incubating the digested muscles with trypsin to dissociate cells; and (4) collecting the dissociated cells by centrifugation and incubating the cells in appropriate medium.

As preferred to the embodiment, the homozygous disruption mice exhibits abnormalities characteristic of developmental disorder such as urinary bladder defects which show hyperplasia of transitional cells and appearance of several degenerative cells in embryo. The homozygous disruption mice also shows abnormalities characteristic of muscular diseases such as diaphragm and tongue atrophy which show sarcoplasmic degeneration and fibrous tissues infiltration compared to the wild type mouse.

The present invention further relates to a transgenic knockout mouse the genome of which is manipulated to comprise a homozygous disruption of hnRNP A1 gene, wherein the mouse exhibits muscle abnormalities characteristic of developmental disorder and muscular diseases as compared to a wild type mouse in which the hnRNP A1 gene is not disrupted.

In the preferred embodiment, the transgenic knockout mouse exhibits lower expression of hnRNP A1 gene as compared to the wild type mouse.

In another preferred embodiment, the disruption of hnRNP A1 gene of the transgenic knockout mouse results in embryonic lethality or immediately dead after birth.

In another preferred embodiment, the disruption of hnRNP A1 gene of the transgenic knockout mouse results in urinary bladder defects which show hyperplasia of transitional cells and appearance of several degenerative cells in an embryo.

In another preferred embodiment, the disruption of hnRNP A1 gene of the transgenic knockout mouse results in diaphragm and tongue atrophy which show sarcoplasmic degeneration and fibrous tissues infiltration in skeletal muscle cell.

The following examples are provided to illustrate the present invention without, however, limiting the same thereto.

EXAMPLES

The process for generating the hnRNP A1 knockout mice and uses thereof of the present disclosure will be illustrated in further detail with reference to several examples below, which are not intended to limit the scope of the present disclosure.

Example 1

The Generation of hnRNP A1 Knockout Mice 1.1 Constructing the Target Vector

The hnRNP A1 targeting vector was generated by deleting exons 2 to 8 of the hnRNP A1 gene. This targeting construct was created using recombineering techniques in a 129S7/AB2.2 bacterial artificial chromosome containing the hnRNP A1 gene (clone bMQ-281N24, Geneservice, Cambridge, UK). A loxP site was inserted before the exon 2 of hnRNP A1. More particularly, the loxP site was inserted between exon 1 and exon 2 of hnRNP A1 gene. A neomycin resistance gene was inserted into the hnRNP A1 gene for the enhancement of selecting positively targeted embryonic stem cells (ES) clones in the presence of neomycin analog G-418. A frt sites flanking the neomycin resistance cassette followed by another loxP site was then inserted behind exon 8. Specifically, "behind exon 8" means between exon 8 and exon 9.

FIG. 1 is a schematic drawing illustrating the constructed vector of Example 1.1 having DNA fragments with exons 2 to 8 of hnRNP A1 being deleted for generating hnRNP A1 knockout mice.

1.2 Selection of Targeted Embryonic Stem (ES) Cell Clones

In order to incorporated the mutated hnRNP A1 gene in the targeting vector into the ES cells for targeting homologous recombination to occur, the targeting construct of Example 1.1 was electroporated into 129 ES cells. The transfected ES cells were then selected by neomycin analog G418. In principle, those ES cells that were targeted and thus carried the mutated hnRNP A1 alleles could survive in the culture environment containing G148 because of the presence of a built-in neomycin resistant gene in the mutated vector. The non-targeted wild type ES cells would die because of the lack of the neomycin gene in the presence of G418.

The surviving targeted ES cells clones were microscopically picked and cultured separately. The individually grown ES cell clones were harvested and isolated for genomic DNAs. The extracted DNAs were analysed on their restriction fragment patterns using genomic Southern blot technology to select for the replacement targeting through homologous recombination and to differentiate it from the unwanted gene insertion events. The neomycin resistance cassette was deleted by introduced Flp recombinase; and the gene segment flanked by the two loxP sites, containing exons from 2 to 8 of hnRNP A1, of the targeted ES cells was deleted by introduced Cre recombinase. The clones showed the band pattern of having 2 site were hnRNP A1 targeted +/− heterozygous knockouts. They were selected for blastocyst injection after expansion.

1.3 Generation of Mouse hnRNP A1 Knockout Line

The targeted ES cell clones of example 1.2 were expanded according to standard procedures. The ES cells were then microinjected into blastocysts recovered from female C57BL/6 mice. The injected blastocysts were re-implanted to female BALB/C mice as foster mothers for the embryos. Approximately 30 to 40 blastocysts were implanted to each foster mother. The foster mothers were maintained in sterile conditions. Litters were born 18-20 days later. Among the newly born pups there were 3 male and 2 female chimeras with different degree of agouti color furs. To determine whether these chimeras had targeted hnRNP A1 ES cells developed into germ cells, the chimeras were mated with the wild-type C57BL/6 mice to generate the F1 mice. The F1's were screened and genotyped for germline transmission.

Figure 2:
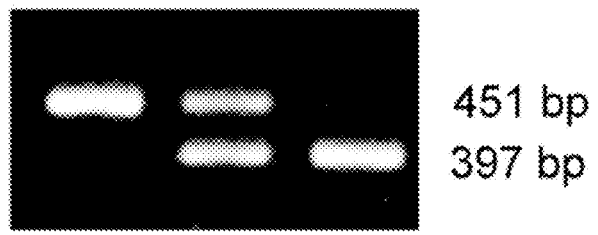
FIG. 2A illustrates the genomic PCR analysis of homozygous (−/−), heterozygous (+/−) and wild-type (+/+) alleles of the F1 mice in accordance with one embodiment of this invention.
FIG. 2B illustrates the expression of hnRNP A1 protein in heart (H) and brain (B) tissues of the F1 mice in accordance with one embodiment of this invention.

PCR methods were used for genotyping the tail DNAs of the mice. The primers, A1U (5'-tatagcgggatgtgacgtgttttg-3', SEQ ID NO: 5) and WT-L (5'-aatgaatcaacaccccgcaacaac-3', SEQ ID NO: 6), were used to show the presence of the wild type allele. The deleted allele was detected by the primers A1U and KO-L (5'-actgcacccacaatgctttaagag-3', SEQ ID NO: 7). Result is depicted in FIG. 2A.

The F1 mice were also analyzed for their expression of hnRNP A1 protein using western blot analysis. Briefly, mouse tissues such as heart and brain, were collected and homogenized in RIPA buffer (50 mM Tris-HCl, pH8, 1 mM EDTA, 150 mM NaCl, 1% NP40, 0.5% sodium deoxycholate, 1% SDS, 1× protease inhibitor cocktails and 1 mM PMSF) at 4° C. for 20 min. The lysates were subjected to SDS-PAGE and immunoblotting. The blots were probed with anti-hnRNP A1 antibody (Sigma, Saint Louis, Mo., USA)) or anti-beta-actin antibody (Santa Cruz, Santa Cruz, Calif., USA) and detected by ECL chemiluminescence kit (GE Healthcare, Piscataway, N.J., USA). Result is depicted in FIG. 2B.

The mice were bred in a specific pathogen-free facility and treated according to the Guide for the Care and Use of Laboratory Animals issued by National Research Council (Taiwan, Republic of China). Embryos of the hnRNP A1 heterozygotes, which were formally named as B6. 129-Hnrnpa1$^{tm1Cfy}$, had been deposited in Rodent Model Resource Center of National Laboratory Animal Center (RMRC-NLAC) in Taiwan with the deposit No. RMRC13102. The hnRNP A1 heterozygotes carrying one deleted allele were interbred to achieve the homozygous hnRNP A1 null mice.

Example 2

Characterization of the hnRNP A1 Knockout Mice 2.1 hnRNP A1$^{-/-}$ Mice Are Embryonic Lethality or Dead After Birth After heterozygous intercross as described in Example 1.3, 18 hnRNP A1$^{+/+}$, 57 hnRNP A1$^{+/-}$ and 8 hnRNP A1$^{-/-}$ pups were born among 10 litters. The heterozygous mice appeared completely normal and fertile. However, the hnRNP A1$^{-/-}$ pups showed small body size and none of homozygous mutant mice was alive after birth. In addition, the number of the homozygous mutant mice was lower than the predicted number of Mendel's Law of Inheritance. These results suggest that a mouse lack of hnRNP A1 results in embryonic lethality or immediately dead after birth.

In order to determine the embryonic lethality, we examined the genotype of embryos at E18.5 from heterozygous intercross. There were 20 hnRNP A1$^{+/+}$, 36 hnRNP A1$^{+/-}$ and 16 hnRNP A$^{-/-}$ embryos at E18.5 among 10 litters. The p value from chi-square analysis is 0.8007. The p value, greater than 0.05, means the genotype of the embryos following Mendel's Law of Inheritance of the ratio 1:2:1. In addition, the body length of hnRNP A1$^{-/-}$ embryos range from 1.0 to 2.1 cm, lower than the average body length of E18.5 (2.2-2.5 cm). This data indicates that the development of hnRNP A1$^{-/-}$ embryos ceased at different developmental ages. Overall, the results support the hypothesis that a mouse lack of hnRNP A1 results in embryonic lethality or immediately dead after birth.

2.2 hnRNP A1$^{-/-}$ Mice Display Embryonic Growth Retardation

Figure 3:
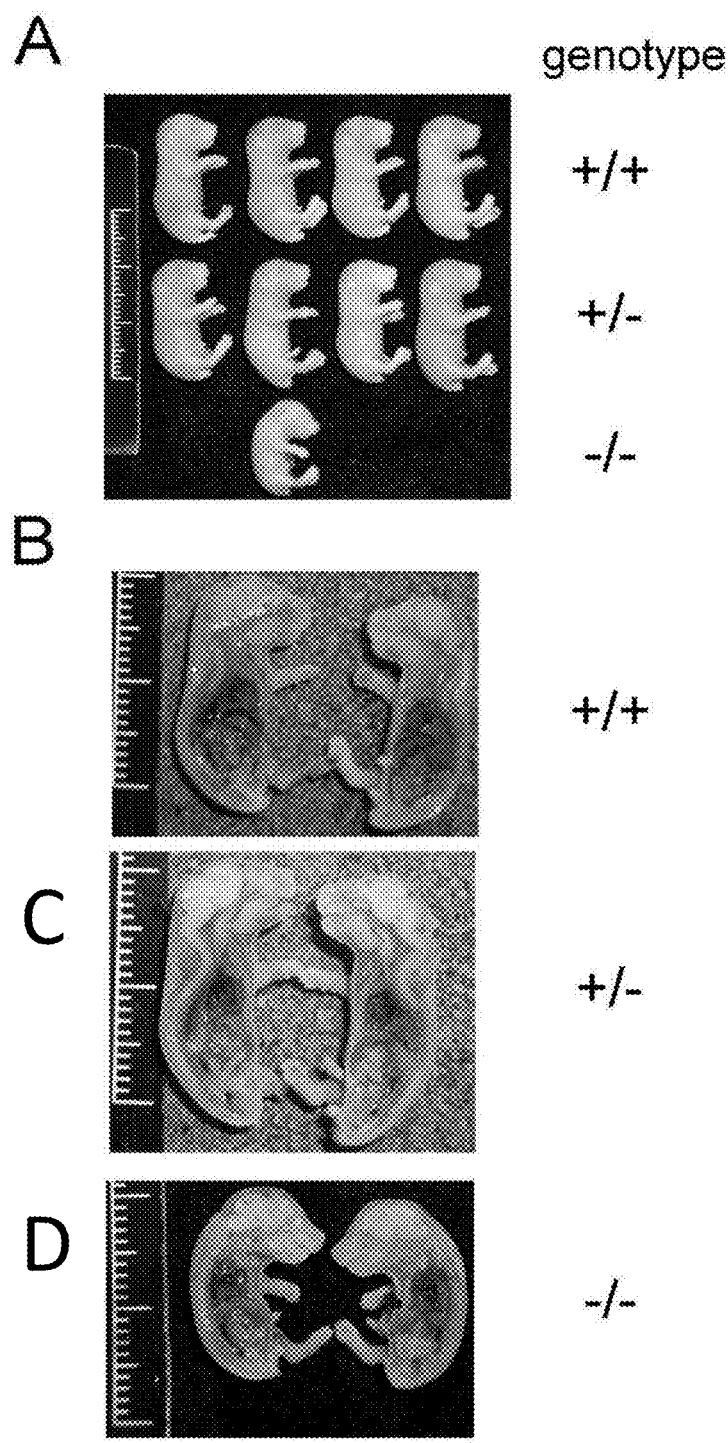
FIG. 3A is a picture showing the external morphology of wild-type (+/+), heterozygous (+/−), and homozygous (−/−) hnRNP A1 knockout embryo at day E18.5 in accordance with one embodiment of this invention.
FIGS. 3B to 3D are pictures showing the sagittal section of wild-type (+/+), heterozygous (+/−), and homozygous (−/−) hnRNP A1 knockout embryo at day E18.5 in accordance with one embodiment of this invention.
Figure 4:
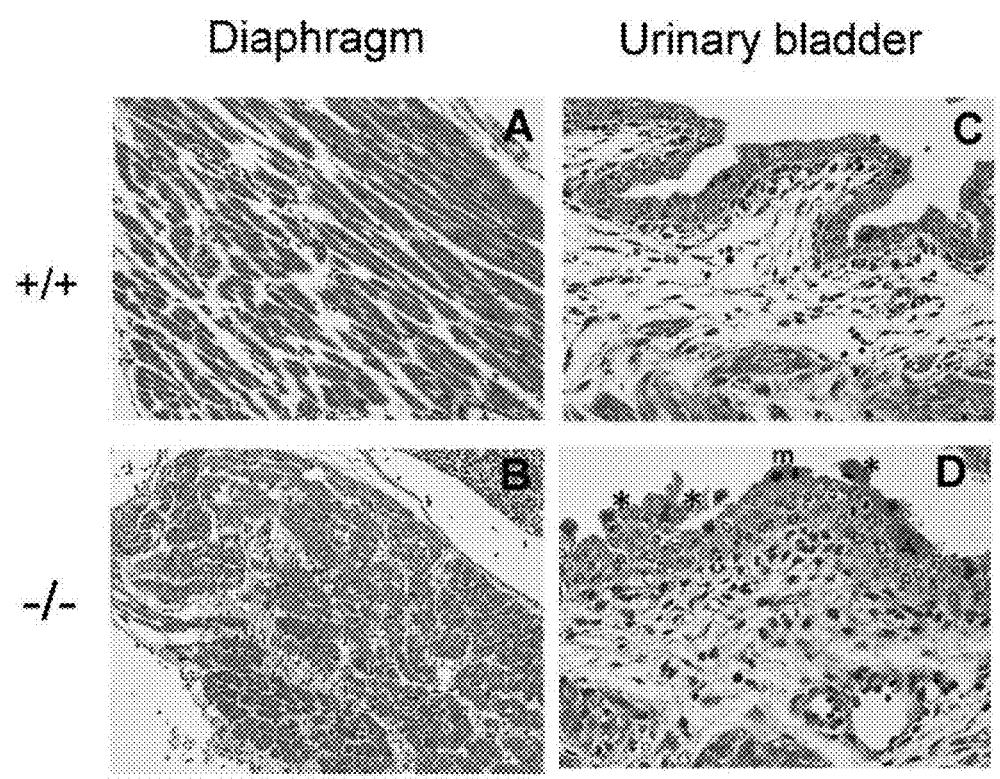
FIG. 4 are histological-staining photographs illustrating the homozygous (−/−) hnRNP A1 knockout mice have diaphragm and urinary bladder defects in accordance with one embodiment of this invention, in which HE staining was performed on the diaphragm and urinary bladder of homozygous (−/−) hnRNP A1 knockout mouse and control mice, and (A) is the diaphragm of normal mouse at E18.5, 200×; (B) is the diaphragm of homozygous (−/−) hnRNP A1 knockout mouse that showed sarcoplasmic degeneration and fibrous tissues infiltration at E18.5, 200×; (C) is the urinary bladder of normal mouse at E18.5, 400×; and (D) is the urinary bladder of homozygous (−/−) hnRNP A1 knockout mouse that showed hyperplasia of transitional cells and appearance of several degenerative cells at E18.5, 400×. "m" represents mitosis, and asterisk represents degenerative cell.

In this example, morphological and histological properties of the hnRNP A1$^{-/-}$ mice at E18.5 were examined. The hnRNP A1$^{-/-}$ embryo displayed growth retardation (FIG. 3A). The internal organs of the hnRNP A1$^{-/-}$ embryo did not appear obviously abnormal (FIG. 3B). Histological analysis were then performed on the embryos. The sections were stained with hematoxylin and eosin (HE). The hnRNP A1$^{-/-}$ mice display diaphragm and urinary bladder defects at E18.5. Histological analysis showed that the diaphragm of hnRNP A1$^{-/-}$ mouse displayed sarcoplasmic degeneration and fibrous tissues infiltration (FIG. 4B) compared with hnRNP A1$^{+/+}$ embryo (FIG. 4A). Moreover, the urinary bladder of hnRNP A1$^{-/-}$ mouse showed hyperplasia of transitional cells and appeared several degenerative cells (FIG. 4D) compared with hnRNP A1$^{+/+}$ embryo (FIG. 4C). These results suggest that a mouse lack of hnRNP A1 results in developmental retardation, which may be multi-organs affected.

2.3 Homozygous hnRNP A1$^{-/-}$ Mice Display Tongue Muscle Degenerate

Figure 5:
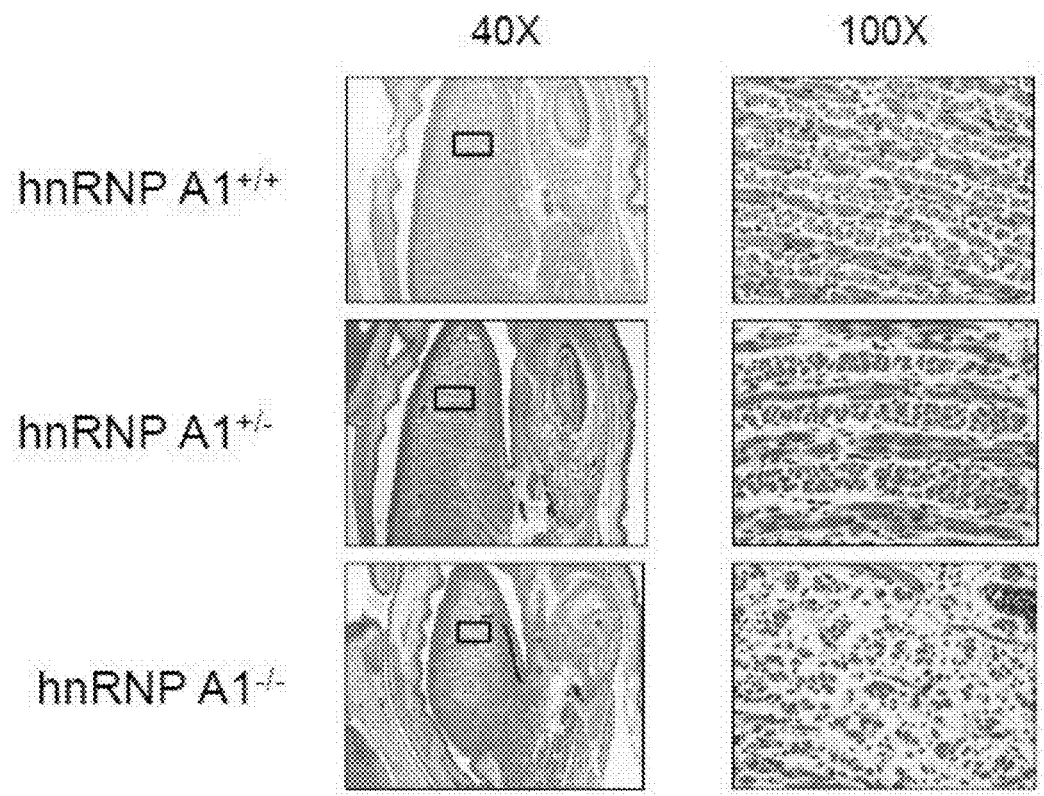
FIG. 5 illustrates histological-staining photographs of the homozygous (−/−) hnRNP A1 knockout mice have tongue defects in accordance with one embodiment of this invention, in which HE staining was performed on the tongue of homozygous (−/−) hnRNP A1 knockout mouse, heterozygous (+/−) hnRNP A1 knockout mouse and (+/+) hnRNP A1 control mice, and left panels from mice at E18.5, 40×; The tissue of homozygous (−/−) hnRNP A1 knockout mouse in the tongue showed loosely. Right panels were images with higher magnification, 100×, of inserted boxes from left panels. The skeletal muscle cells of homozygous (−/−) hnRNP A1 knockout mouse showed degenerated.

In this example, histological properties of the hnRNP A1$^{-/-}$ mice at E18.5 were examined. The homozygous (−/−) hnRNP A1 knockout mice have tongue defects in accordance with one embodiment of this invention (FIG. 5), in which HE staining was performed on the tongue of homozygous (−/−) hnRNP A1 knockout mouse, heterozygous (+/−) hnRNP A1 knockout mouse and (+/+) hnRNP A1 control mice, and left panels from mice at E18.5, 40×; The tissue of homozygous (−/−) hnRNP A1 knockout mouse in the tongue showed loosely. Right panels were images with higher magnification, 100×, of inserted boxes from left panels. The skeletal muscle cells of homozygous (−/−) hnRNP A1 knockout mouse showed degenerated appearance. These results suggest that a mouse lack of hnRNP A1 results in tongue atrophy which show degenerated skeletal muscle cell compared to the wild type mouse.

Figure 6:
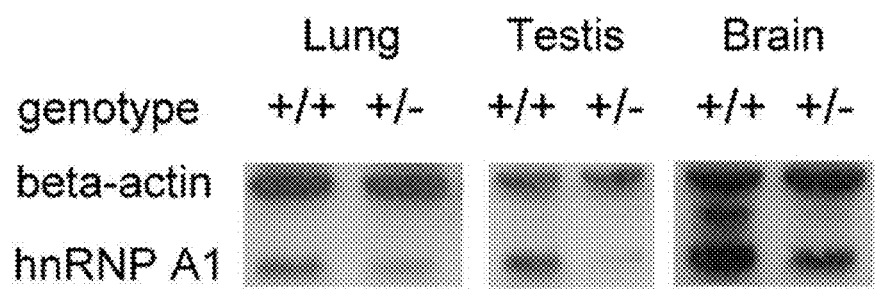
FIG. 6 illustrates the amount of hnRNP A1 protein expressed in organs of wild-type (+/+) mouse and heterozygous (+/−) hnRNP A1 knockout adult mouse in accordance with one embodiment of this invention, in which the hnRNP A1 protein from lung, testis and brain of wild-type (+/+) mouse and heterozygous (+/−) hnRNP A1 knockout adult mouse was detected by Western blot and beta-actin was used as loading control.

2.4 Heterozygous hnRNP A1$^{+/-}$ Adult Mice Express Low hnRNP A1 Protein in Organs Since the gene number of hnRNP A1 in heterozygous hnRNP A1$^{+/-}$ adult mice are lower than homozygous hnRNP A1$^{+/+}$ mice. The protein levels of hnRNP A1 in the organs of these mice were determined. The organs, such lung, testis and brain, from these mice were collected and using Western blot to detect the amount of hnRNP A1 protein. The results showed that heterozygous hnRNP A1$^{+/-}$ adult mice expressed lower hnRNP A1 protein than hnRNP A1$^{+/+}$ mice in these organs (FIG. 6). These result results demonstrate that even with the normal phenotype, the heterozygous hnRNP A1$^{+/-}$ adult mice express low hnRNP A1 protein in some organs.

It will be understood that the above description of embodiments is given by way of example only and that various modifications may be made by those with ordinary skill in the art. The above specification, examples and data provide a complete description of the structure and use of exemplary embodiments of the invention. Although various embodiments of the invention have been described above with a certain degree of particularity, or with reference to one or more individual embodiments, those with ordinary skill in the art could make numerous alterations to the disclosed embodiments without departing from the spirit or scope of this invention. All publication, patents and patent application are herein incorporated by reference in their entirety to the same extent as if each individual publication, patent or patent application was specifically and individually indicated to be incorporated by reference in its entirety.

What is claimed is:

1. A transgenic knockout mouse the whose genome is manipulated to comprise a homozygous disruption of hnRNP A1 gene, wherein the mouse exhibits tongue atrophy as compared to a wild-type mouse in which the hnRNP A1 gene is not disrupted, wherein said homozygous disruption of hnRNP A1 gene comprising deletion of exons 2-8 of the hnRNP A1 gene, wherein the mouse exhibits no expression of hnRNP A1 gene, wherein the tongue atrophy comprises degenerated skeletal muscle cells.

* * * * *